United States Patent
Haag et al.

(10) Patent No.: US 9,822,203 B2
(45) Date of Patent: Nov. 21, 2017

(54) METHOD FOR PRODUCING WATER-ABSORBING POLYMER PARTICLES WITH HIGH SWELLING RATE AND HIGH CENTRIFUGE RETENTION CAPACITY WITH SIMULTANEOUSLY HIGH PERMEABILITY OF THE SWOLLEN GEL BED

(71) Applicant: BASF SE, Ludwigshafen (DE)

(72) Inventors: Monica Haag, Ludwigshafen (DE); Roland Krauss, Neustadt (DE); Thomas Gieger, Ludwigshafen (DE); Volker Klock, Ludwigshafen (DE); Matthias Weismantel, Jossgrund-Oberndorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/763,185

(22) PCT Filed: Jan. 20, 2014

(86) PCT No.: PCT/EP2014/050980
§ 371 (c)(1),
(2) Date: Jul. 24, 2015

(87) PCT Pub. No.: WO2014/118024
PCT Pub. Date: Aug. 7, 2014

(65) Prior Publication Data
US 2015/0376318 A1     Dec. 31, 2015

(30) Foreign Application Priority Data
Jan. 29, 2013  (EP) .................... 13152994

(51) Int. Cl.
| | | |
|---|---|---|
| *C08F 2/10* | (2006.01) | |
| *C08F 222/10* | (2006.01) | |
| *C08F 6/00* | (2006.01) | |
| *C08F 8/00* | (2006.01) | |
| *C08J 3/24* | (2006.01) | |
| *A61L 15/60* | (2006.01) | |
| *C08F 220/06* | (2006.01) | |

(52) U.S. Cl.
CPC ........ *C08F 222/1006* (2013.01); *A61L 15/60* (2013.01); *C08F 2/10* (2013.01); *C08F 220/06* (2013.01); *C08J 3/245* (2013.01); *C08J 2333/02* (2013.01)

(58) Field of Classification Search
None
See application file for complete search history.

(56) References Cited

U.S. PATENT DOCUMENTS

| 6,710,141 B1 | 3/2004 | Heide et al. | |
|---|---|---|---|
| 2005/0051925 A1* | 3/2005 | Gartner | B01J 3/006 264/211.24 |
| 2008/0004408 A1 | 1/2008 | Stueven et al. | |
| 2008/0080300 A1 | 4/2008 | Stueven et al. | |
| 2011/0015362 A1 | 1/2011 | Weismantel et al. | |
| 2012/0302714 A1* | 11/2012 | Weismantel | C08F 2/001 526/318.42 |
| 2013/0102750 A1* | 4/2013 | Watanabe | C08F 6/008 526/318.41 |

FOREIGN PATENT DOCUMENTS

| EP | 0 497 623 A2 | 8/1992 |
|---|---|---|
| WO | WO-01/38402 A1 | 5/2001 |
| WO | WO-03/022896 A1 | 3/2003 |
| WO | WO-03/051415 A1 | 6/2003 |
| WO | WO-2005/097313 A1 | 10/2005 |
| WO | WO-2006/034806 A1 | 4/2006 |
| WO | WO-2006/034853 A1 | 4/2006 |
| WO | WO-2009/115472 A1 | 9/2009 |
| WO | WO-2012/107432 A1 | 8/2012 |
| WO | WO-2012/119969 A1 | 9/2012 |
| WO | WO-2012/160174 A1 | 11/2012 |
| WO | WO-2013/007819 A1 | 1/2013 |

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.
International Search Report in International Application No. PCT/EP2014/050980, dated May 6, 2014.

* cited by examiner

*Primary Examiner* — Jeffrey Mullis
(74) *Attorney, Agent, or Firm* — Marshall, Gerstein & Borun LLP

(57) ABSTRACT

A process for producing water-absorbing polymer particles having high free swell rate and high centrifuge retention capacity with simultaneously high permeability of the swollen gel bed by polymerization of an aqueous monomer solution in a polymerization reactor having at least two shafts (kneaders) which rotate in an axially parallel manner, subsequent extrusion at high temperatures and thermal surface postcrosslinking.

20 Claims, No Drawings

METHOD FOR PRODUCING WATER-ABSORBING POLYMER PARTICLES WITH HIGH SWELLING RATE AND HIGH CENTRIFUGE RETENTION CAPACITY WITH SIMULTANEOUSLY HIGH PERMEABILITY OF THE SWOLLEN GEL BED

CROSS-REFERENCE TO RELATED APPLICATIONS

This application is the U.S. National Phase of PCT Application No. PCT/EP2014/050980, filed Jan. 20, 2014, which claims the benefit of European patent application No. 13152994.3, filed Jan. 29, 2013.

The present invention relates to a process for producing water-absorbing polymer particles having high free swell rate (FSR) and high centrifuge retention capacity (CRC) with simultaneously high permeability of the swollen gel bed by polymerization of an aqueous monomer solution in a polymerization reactor having at least two shafts (kneaders) which rotate in an axially parallel manner, subsequent extrusion at high temperatures and thermal surface postcrosslinking.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With an increasing amount of crosslinker, the centrifuge retention capacity (CRC) falls and the absorption under a pressure of 21.0 g/cm$^2$ (AUL0.3 psi) passes through a maximum.

To improve the use properties, for example, permeability of the swollen gel bed (SFC) in the diaper and absorption under a pressure of 49.2 g/cm$^2$ (AUL0.7 psi), water-absorbing polymer particles are generally surface postcrosslinked. This increases the level of crosslinking of the particle surface, which can at least partly decouple the absorption under a pressure of 49.2 g/cm$^2$ (AUL0.7 psi) and the centrifuge retention capacity (CRC). This surface postcrosslinking can be performed in aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the water-absorbing polymer particles.

The production of water-absorbing polymer particles in a polymerization reactor with at least two axially parallel rotating shafts (kneaders) is described, for example, in WO 01/038402 A1, WO 03/022896 A1, WO 03/051415 A1, WO 2006/034806 A1, WO 2006/034853 A1 and WO 2009/115472 A1.

The extrusion of the polymer gels which form in the polymerization is described in EP 0 497 623 A2.

WO 2005/097313 A1 discloses water-absorbing polymer particles with high free swell rate (FSR).

It was an object of the present invention to provide an improved process for producing water-absorbing polymer particles, especially water-absorbing polymer particles with high free swell rate (FSR) and high centrifuge retention capacity (CRC) with simultaneously high permeability of the swollen gel bed (SFC).

The object was achieved by a process for producing water-absorbing polymer particles by polymerizing a monomer solution or suspension comprising a) an ethylenically unsaturated monomer which bears acid groups and may be at least partly neutralized,
b) at least one crosslinker,
c) at least one initiator,
d) optionally an ethylenically unsaturated monomer copolymerizable with the monomers mentioned under a) and
e) optionally one or more water-soluble polymers, in a polymerization reactor having at least two shafts (kneaders) rotating in an axially parallel manner, drying the resulting polymer gel, grinding the dried polymer gel, classifying and thermally surface postcrosslinking, which process comprises using at least 0.25% by weight of the crosslinker b), based on the unneutralized monomer a), extruding the polymer gel prior to drying, the polymer gel during the extrusion having a temperature greater than 80° C. and less than 60 kWh/t of specific mechanical energy being introduced in the course of extrusion.

During the extrusion, the polymer gel has a temperature of preferably greater than 85° C., more preferably greater than 90° C., most preferably greater than 92° C. During the extrusion, the polymer gel has a temperature of preferably less than 150° C., more preferably less than 120° C., most preferably less than 105° C.

In order to prevent cooling of the polymer gel during the extrusion, the extruder is preferably trace-heated, more preferably with steam.

The ratio of length to diameter of the extruder is preferably less than 6, more preferably less than 5.5, most preferably less than 5. Thus, it is advantageous to use short extruders. As a result, excessively high pressures in the extrusion are avoided.

In the course of extrusion, the polymer gel is forced through the holes of a perforated plate. The diameter of the holes is in the range from preferably 2 to 20 mm, more preferably 5 to 15 mm and most preferably 8 to 12 mm.

The orifice ratio of the perforated plate, i.e. the ratio of the sum of the area of the hole orifices to the total area of the perforated plate, is in the range from preferably 5 to 50%, more preferably 7 to 30% and most preferably 10 to 20%.

The thickness of the perforated plate, i.e. the length of the holes in the perforated plate, is in the range from preferably 5 to 50 mm, more preferably 10 to 40 mm and most preferably 15 to 35 mm.

The pressure bearing on the perforated plate is in the range from preferably 5 to 50 bar, more preferably 10 to 40 bar and most preferably 15 to 35 bar.

The specific mechanical energy (SME) introduced in the course of extrusion is preferably from 2 to 60 kWh/t, more preferably from 5 to 50 kWh/t and most preferably from 10 to 40 kWh/t, and can be influenced, for example, via the ratio of internal length to internal diameter of the extruder (L/D). The specific mechanical energy (SME) is the motor output of the extruder in kW divided by the throughput of polymer gel in t/h.

In a preferred embodiment of the present invention, the polymerization is performed in the presence of an inert gas and under elevated pressure.

Suitable inert gases are nitrogen, carbon dioxide, steam and argon. The polymerization reaction is inhibited by oxygen. Therefore, the inert gas should comprise preferably less than 0.001% by volume, more preferably less than 0.0005% by volume and most preferably less than 0.0002% by volume of oxygen. Advantageously, the inert gas flows continuously through the polymerization reactor. The inert gas volume flow rate is preferably from 0.001 to 5 m$^3$/h per m$^3$ of reactor volume, more preferably from 0.01 to 2 m$^3$/h per m$^3$ of reactor volume and most preferably from 0.2 to 1 m$^3$/h per m$^3$ of reactor volume.

The inert gas used is preferably nitrogen, more preferably in technical grade quality. Technical grade nitrogen comprises typically at least 99.8% by volume of nitrogen and less than 0.0005% by volume of oxygen.

The gauge pressure in the polymerization reactor is preferably from 1 to 500 mbar, more preferably from 5 to 100 mbar and most preferably from 10 to 30 mbar.

The polymerization reactors usable in the process according to the invention have at least two axially parallel rotating shafts, typically with several kneading and transport elements present on the shafts.

Polymerization reactors usable in the process according to the invention are available, for example, from List AG (Arisdorf; Switzerland) and are described in CH 664 704 A5, EP 0 517 068 A1, WO 97/12666 A1, DE 21 23 956 A1, EP 0 603 525 A1, DE 195 36 944 A1 and DE 41 18 884 A1.

Such polymerization reactors having at least two shafts achieve, by virtue of the arrangement of the kneading and transport elements, a high level of self-cleaning, which is an important requirement for a continuous polymerization. The two shafts preferably rotate counter to one another.

On the stirrer shaft, the disk segments are arranged in the manner of a propeller. Suitable kneading and transport elements are, for example, close-clearance mixing bars and L- or U-shaped attachments.

The present invention is based on the finding that the properties of water-absorbing polymer particles can be improved when relatively highly crosslinked polymer gels are additionally extruded at relatively high temperatures in the polymerization reactor having at least two shafts which rotate in an axially parallel manner. The shear forces which occur lead to rougher polymer particles, which have a high free swell rate (FSR) and a high centrifuge retention capacity (CRC) after the thermal surface postcrosslinking. To date, the increase in the free swell rate (FSR) has always led to a lowering of the centrifuge retention capacity (CRC) with comparable permeability of the swollen gel bed (SFC), or to a lowering of the permeability of the swollen gel bed (SFC) with comparable centrifuge retention capacity (CRC).

Excessively high energy inputs in the course of extrusion, however, lead to a deterioration in the free swell rate (FSR) and in the centrifuge retention capacity (CRC) and should therefore be avoided.

The production of the water-absorbing polymer particles is described in detail hereinafter:

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.25 to 1.5% by weight, more preferably 0.3 to 1.2% by weight and most preferably 0.4 to 0.8% by weight, based in each case on unneutralized monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose. Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

The polymer gel is then preferably dried with a belt drier until the residual moisture content is preferably 0.5 to 15% by weight, more preferably 1 to 10% by weight and most preferably 2 to 8% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 and 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two-stage or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles having a particle size of greater than 150 µm is preferably at least 90% by weight, more preferably at least 95% by weight and most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization. However, it is also possible to incorporate the excessively small polymer particles into the polymer gel in an extruder connected downstream of the polymerization reactor.

If the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight. Polymer particles of excessively large particle size lower the free swell rate. The proportion of excessively large polymer particles should therefore likewise be low.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.01 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact driers, more preferably shovel driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred reaction temperatures are in the range of 100 to 250° C., preferably 120 to 220° C., more preferably 130 to 210° C. and most preferably 150 to 200° C. The preferred residence time at this temperature is preferably at least 10 minutes, more preferably at least 20 minutes, most preferably at least 30 minutes, and typically at most 60 minutes.

In a preferred embodiment of the present invention, the water-absorbing polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Coolers (Hosokawa Micron GmbH; Leingarten; Germany), Hosokawa Bepex® Disc Coolers (Hosokawa Micron GmbH; Leingarten; Germany), Holo-Flite® coolers (Metso Minerals Industries Inc.; Danville; USA) and Nara Paddle Coolers (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging. The remoisturizing is advantageously performed in the cooler after the thermal drying.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides water-absorbing polymer particles obtainable by polymerizing a monomer solution or suspension comprising
a) an ethylenically unsaturated monomer which bears acid groups and may be at least partly neutralized,
b) at least one crosslinker,
c) at least one initiator,
d) optionally an ethylenically unsaturated monomer copolymerizable with the monomers mentioned under a) and
e) optionally one or more water-soluble polymers, wherein at least 0.25% by weight of the crosslinker b), based on the unneutralized monomer a), has been used, and wherein the resulting polymer gel has been extruded, the water-absorbing polymer particles have been thermally surface postcrosslinked, the water-absorbing polymer particles have a free swell rate of at least 0.25 g/g s, a centrifuge retention capacity of at least 20 g/g, an absorption under a pressure of 49.2 g/cm$^2$ of at least 20 g/g and a saline flow conductivity of at least $100 \times 10^{-7}$ cm$^3$ s/g.

The amount of crosslinker b) is preferably 0.25 to 1.5% by weight, more preferably 0.3 to 1.2% by weight and most preferably 0.4 to 0.8% by weight, based in each case on unneutralized monomer a).

The inventive water-absorbing polymer particles have a free swell rate (FSR) of typically at least 0.25 g/g s, preferably at least 0.27 g/g s, more preferably at least 0.29 g/g s and most preferably at least 0.3 g/g s. The free swell rate (FSR) of the water-absorbing polymer particles is typically less than 1.0 g/g s.

The inventive water-absorbing polymer particles have a centrifuge retention capacity (CRC) of typically at least 20 g/g, preferably at least 22 g/g, more preferably at least 23 g/g and most preferably at least 25 g/g. The centrifuge retention capacity (CRC) of the water-absorbing polymer particles is typically less than 60 g/g. The centrifuge retention capacity (CRC) is determined by EDANA recommended test method No. WSP 241.2-05 "Fluid Retention Capacity in Saline, After Centrifugation".

The inventive processes water-absorbing polymer particles have an absorption under a pressure of 49.2 g/cm$^2$ (AUL0.7 psi) of typically at least 20 g/g, preferably at least 21 g/g, more preferably at least 22 g/g, especially preferably at least 23 g/g and most preferably at least 24 g/g. The absorption under a pressure of 49.2 g/cm$^2$ (AUL0.7 psi) of the water-absorbing polymer particles is typically less than 35 g/g. The absorption under a pressure of 49.2 g/cm$^2$ (AUL0.7 psi) is determined analogously to EDANA recommended test method No. WSP 242.2-05 "Absorption Under Pressure, Gravimetric Determination", except that a pressure of 49.2 g/cm$^2$ is established instead of a pressure of 21.0 g/cm$^2$.

The inventive water-absorbing polymer particles have a saline flow conductivity (SFC) of typically at least $100 \times 10^{-7}$ cm$^3$ s/g, preferably at least $110 \times 10^{-7}$ cm$^3$ s/g, more preferably $120 \times 10^{-7}$ cm$^3$ s/g and most preferably $130 \times 10^{-7}$ cm$^3$ s/g. The saline flow conductivity (SFC) of the water-absorbing polymer particles is typically less than $500 \times 10^{-7}$ cm$^3$ s/g.

The inventive water-absorbing polymer particles have a proportion of particles having a particle size of 300 to 600 μm of preferably at least 30% by weight, more preferably at least 40% by weight and most preferably at least 50% by weight.

The present invention further provides hygiene articles comprising inventive water-absorbing polymer particles.

The hygiene articles typically comprise a water-impervious backside, a water-pervious topside and an intermediate absorbent core composed of the inventive water-absorbing polymer particles and fibers, preferably cellulose. The proportion of the inventive water-absorbing polymer particles in the absorbent core is preferably 20 to 100% by weight and more preferably 50 to 100% by weight.

Methods:

The standard test methods described hereinafter and designated "WSP" are described in: "Standard Test Methods for the Nonwovens Industry", 2005 edition, published jointly by the Worldwide Strategic Partners EDANA (Avenue Eugène Plasky, 157, 1030 Brussels, Belgium, www.edana.org) and INDA (1100 Crescent Green, Suite 115, Cary, N.C. 27518, U.S.A., www.inda.org). This publication is available both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Fluid Retention Capacity in Saline, After Centrifugation".

Absorption Under a Pressure of 21.0 g/cm² (Absorption Under Load)

The absorption under a pressure of 21.0 g/cm² (AUL0.3 psi) is determined by EDANA recommended test method No. WSP 242.2-05 "Absorption Under Pressure, Gravimetric Determination".

Absorption Under a Pressure of 49.2 g/cm² (Absorption Under Load)

The absorption under a pressure of 49.2 g/cm² (AUL0.7 psi) is determined analogously to EDANA recommended test method No. WSP 242.2-05 "Absorption Under Pressure, Gravimetric Determination", except that a pressure of 49.2 g/cm² (AUL0.7 psi) is established rather than a pressure of 21.0 g/cm² (AUL0.3 psi).

Free Swell Rate

To determine the free swell rate (FSR), 1.00 g (=$W_1$) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=$W_2$). The time interval required for the absorption, which has been measured with the stopwatch, is designated as t. The disappearance of the last liquid droplet on the surface is determined as the time t.

The free swell rate (FSR) is calculated therefrom as follows:

$$FSR\ [g/g\ s]=W_2/(W_1 \times t)$$

If the moisture content of the water-absorbing polymer particles, however, is more than 3% by weight, the weight $W_1$ should be corrected to take account of this moisture content.

For the determination of the free swell rate (FSR) of the base polymer, only the particle size fraction from 300 to 400 μm is used.

Saline Flow Conductivity

The saline flow conductivity (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the cited patent application having been modified such that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$SFC\ [cm^3\ s/g]=(Fg(t=0) \times L_0)/(d \times A \times WP)$$

where $Fg(t=0)$ is the flow of NaCl solution in g/s, which is obtained using linear regression analysis of the $Fg(t)$ data of the flow determinations by extrapolation to $t=0$, $L_0$ is the thickness of the gel layer in cm, d is the density of the NaCl solution in g/cm³, A is the area of the gel layer in cm², and WP is the hydrostatic pressure over the gel layer in dyn/cm².

EXAMPLES

Example 1

By continuously mixing water, 50% by weight sodium hydroxide solution and acrylic acid, a 42.7% by weight acrylic acid/sodium acrylate solution was prepared such that the degree of neutralization was 69.0 mol %. After the components had been mixed, the monomer solution was cooled continuously to a temperature of 30° C. by means of a heat exchanger and degassed with nitrogen. The polyethylenically unsaturated crosslinker used was 3-tuply ethoxylated glyceryl triacrylate (purity approx. 85% by weight). The amount used, based on the acrylic acid (boaa) used, was 0.35% by weight. To initiate the free-radical polymerization, the following components were used: 0.0008% by weight boaa of hydrogen peroxide, metered in as a 2.5% by weight aqueous solution, 0.13% by weight boaa of sodium peroxodisulfate, metered in as a 15% by weight aqueous solution, and 0.0023% by weight boaa of ascorbic acid, metered in as a 0.5% by weight aqueous solution. The throughput of the monomer solution was 800 kg/h.

The individual components were metered continuously into a List ORP 250 Contikneter continuous kneader reactor (List AG, Arisdorf, Switzerland). In the first third of the reactor, 26.3 kg/h of removed undersize with a particle size of less than 150 μm were additionally added. The reaction solution had a feed temperature of 30° C. The residence time of the reaction mixture in the reactor was approx. 15 minutes.

Some of the polymer gel thus obtained was extruded with an SLRE 75 R extruder (Sela Maschinen GmbH; Harbke; Germany). The temperature of the polymer gel in the course of extrusion was 95° C. The perforated plate had 12 holes having a hole diameter of 8 mm. The thickness of the perforated plate was 16 mm. The ratio of internal length to internal diameter of the extruder (L/D) was 4. The specific mechanical energy (SME) of the extrusion was 26 kWh/t. The extruded polymer gel was distributed on metal sheets and dried at 175° C. in an air circulation drying cabinet for 90 minutes. The loading of the metal sheets with polymer gel was 0.81 g/cm².

The dried polymer gel was ground by means of a one-stage roll mill (three milling runs, 1st milling run with gap width 1000 μm, 2nd milling run with gap width 600 μm and 3rd milling run with gap width 400 μm). The ground dried polymer gel was classified and a synthetic particle size distribution (PSD) with the following composition was mixed:

600 to 710 μm: 10.6% by weight
500 to 600 μm: 27.9% by weight
300 to 500 μm: 42.7% by weight
200 to 300 μm: 13.8% by weight
150 to 200 μm: 5.0% by weight The base polymer A thus obtained was analyzed. The results are entered in table 1.

Example 2

1.2 kg of base polymer A from example 1 were coated in a Pflugschar M5 plowshare mixer with heating jacket (Gebr. Lödige Maschinenbau GmbH; Paderborn, Germany) at 23° C. and a shaft speed of 200 revolutions per minute by means of a two-substance spray nozzle with 54.6 g of a mixture of 0.07% by weight of N-hydroxyethyl-2-oxazolidinone, 0.07% by weight of 1,3-propanediol, 0.7% by weight of propylene glycol, 2.27% by weight of a 22% by weight aqueous aluminum lactate solution, 0.448% by weight of a 0.9% by weight aqueous sorbitan monolaurate solution and 0.992% by weight of isopropanol, the percentages by weight each being based on base polymer A.

After the spray application, the product temperature was increased to 185° C. and the reaction mixture was held at this temperature and a shaft speed of 50 revolutions per minute for 35 minutes. The resulting product was cooled to ambient temperature and classified again with a 710 μm sieve. The fraction with a particle size of less than 710 μm was analyzed. The results are entered in table 2.

Example 3 (Comparative Example)

The procedure was as in example 1, except that the resulting polymer gel was not extruded. The base polymer B thus obtained was analyzed. The results are entered in table 1.

Example 4 (Comparative Example)

The base polymer B from example 3 was thermally surface postcrosslinked as in example 2. The fraction with a particle size of less than 710 μm was analyzed. The results are entered in table 2.

Example 5

The procedure was as in example 1, except that the temperature of the polymer gel in the course of extrusion was 85°. The base polymer C thus obtained was analyzed. The results are entered in table 1.

Example 6

The base polymer C from example 5 was thermally surface postcrosslinked as in example 2. The fraction with a particle size of less than 710 μm was analyzed. The results are entered in table 2.

Example 7 (Comparative Example)

The procedure was as in example 1, except that the temperature of the polymer gel in the course of extrusion was 62°. The base polymer D thus obtained was analyzed. The results are entered in table 1.

Example 8 (Comparative Example)

The base polymer D from example 7 was thermally surface postcrosslinked as in example 2. The fraction with a particle size of less than 710 μm was analyzed. The results are entered in table 2.

TABLE 1

Influence of polymer gel temperature in the course of extrusion on the base polymer

| Ex. | Polymer gel temp. [° C.] | CRC [g/g] | AUL0.3 psi [g/g] | FSR [g/gs] |
|---|---|---|---|---|
| 3*) | — | 37.7 | 11.0 | 0.31 |
| 1 | 95 | 34.4 | 16.4 | 0.38 |
| 5 | 85 | 34.2 | 17.0 | 0.37 |
| 7*) | 62 | 37.2 | 10.3 | 0.25 |

*)comparative examples

TABLE 2

Influence of polymer gel temperature in the course of extrusion on the end product

| Ex. | Polymer gel temp. [° C.] | SFC [10-7 × cm$^3$s/g] | CRC [g/g] | AUL0.7 psi [g/g] | FSR [g/gs] |
|---|---|---|---|---|---|
| 4*) | — | 76 | 27.7 | 25.1 | 0.17 |
| 2 | 95 | 103 | 27.2 | 25.1 | 0.34 |
| 6 | 85 | 98 | 26.7 | 24.9 | 0.29 |
| 8*) | 62 | 95 | 27.0 | 23.8 | 0.22 |

*)comparative examples

Examples 1 to 8 show that the free swell rate (FSR) after surface postcrosslinking rises with the polymer gel temperature during extrusion.

Example 9 (Comparative Example)

By continuously mixing water, 50% by weight sodium hydroxide solution and acrylic acid, a 42.7% by weight acrylic acid/sodium acrylate solution was prepared such that the degree of neutralization was 69.0 mol %. After the components had been mixed, the monomer solution was cooled continuously to a temperature of 30° C. by means of a heat exchanger and degassed with nitrogen. The polyethylenically unsaturated crosslinker used was 3-tuply ethoxylated glyceryl triacrylate (purity approx. 85% by weight). The amount used, based on the acrylic acid used, was 0.20% by weight. To initiate the free-radical polymerization, the following components were used: 0.002% by weight boaa of hydrogen peroxide, metered in as a 2.5% by weight aqueous solution, 0.1% by weight boaa of sodium peroxodisulfate, metered in as a 15% by weight aqueous solution, and 0.01% by weight boaa of ascorbic acid, metered in as a 0.5% by weight aqueous solution. The throughput of the monomer solution was 40 kg/h.

The individual components were metered continuously into a List ORP 10 Contikneter continuous kneader reactor (List AG, Arisdorf, Switzerland).

The reaction solution had a feed temperature of 30° C. The residence time of the reaction mixture in the reactor was approx. 15 minutes.

Some of the polymer gel thus obtained was extruded with an SLRE 75 R extruder (Sela Maschinen GmbH; Harbke; Germany). The temperature of the polymer gel in the course of extrusion was 85° C. The perforated plate had 12 holes having a hole diameter of 8 mm. The thickness of the perforated plate was 16 mm. The ratio of internal length to internal diameter of the extruder (L/D) was 4. The specific mechanical energy (SME) of the extrusion was 26 kWh/t. The extruded polymer gel was distributed on metal sheets and a and dried at 175° C. in an air circulation drying cabinet for 90 minutes. The loading of the metal sheets with polymer gel was 0.81 g/cm$^2$.

The dried polymer gel was ground by means of a one-stage roll mill (three milling runs, 1st milling run with gap width 1000 μm, 2nd milling run with gap width 600 μm and 3rd milling run with gap width 400 μm). The ground dried polymer gel was classified and a synthetic particle size distribution (PSD) with the following composition was mixed:
600 to 710 μm: 10.6% by weight
500 to 600 μm: 27.9% by weight
300 to 500 μm: 42.7% by weight
200 to 300 μm: 13.8% by weight
150 to 200 μm: 5.0% by weight The base polymer E thus obtained was analyzed. The results are entered in table 3.

Example 10 (Comparative Example)

The base polymer E from example 9 was thermally surface postcrosslinked as in example 2. The fraction with a particle size of less than 710 μm was analyzed. The results are entered in table 4.

Example 11

The procedure was as in example 9, except that the amount of the crosslinker used, based on the acrylic acid used, was 0.28% by weight. The base polymer F thus obtained was analyzed. The results are entered in table 3.

Example 12

The base polymer F from example 11 was thermally surface postcrosslinked as in example 2. The fraction with a particle size of less than 710 μm was analyzed. The results are entered in table 4.

Example 13

The procedure was as in example 9, except that the amount of the crosslinker used, based on the acrylic acid used, was 0.35% by weight. The base polymer G thus obtained was analyzed. The results are entered in table 3.

Example 14

The base polymer G from example 13 was thermally surface postcrosslinked as in example 2. The fraction with a particle size of less than 710 μm was analyzed. The results are entered in table 4.

Example 15

The procedure was as in example 1, except that the amount of the crosslinker used, based on the acrylic acid used, was 0.43% by weight. The temperature of the polymer gel in the course of extrusion was 85°. The base polymer H thus obtained was analyzed. The results are entered in table 3.

Example 16

The base polymer H from example 15 was thermally surface postcrosslinked as in example 2. The fraction with a particle size of less than 710 μm was analyzed. The results are entered in table 4.

TABLE 3

Influence of crosslinker on the base polymer

| Ex. | Crosslinker [% by wt.] | CRC [g/g] | AUL0.3 psi [g/g] | FSR [g/gs] |
|---|---|---|---|---|
| 9*) | 0.20 | 37.3 | 8.8 | 0.31 |
| 11 | 0.28 | 34.3 | 11.8 | 0.35 |
| 13 | 0.35 | 33.5 | 15.1 | 0.35 |
| 15 | 0.43 | 32.5 | 22.9 | 0.40 |

*)comparative examples

TABLE 4

Influence of crosslinker on the end product

| Ex. | Crosslinker [% by wt.] | SFC [$10^{-7} \times cm^3 s/g$] | CRC [g/g] | AUL0.7 psi [g/g] | FSR [g/gs] |
|---|---|---|---|---|---|
| 10*) | 0.20 | 106 | 25.8 | 23.2 | 0.24 |
| 12 | 0.28 | 121 | 26.4 | 25.0 | 0.26 |
| 14 | 0.35 | 135 | 26.3 | 23.9 | 0.29 |
| 16 | 0.43 | 122 | 26.4 | 24.6 | 0.32 |

*)comparative examples

Examples 9 to 16 show that the free swell rate (FSR) after surface postcrosslinking rises with the amount of crosslinker used in the extruded base polymers.

Example 17 (Comparative Example)

The procedure was as in example 9, except that the resulting polymer gel was not extruded. The base polymer I thus obtained was analyzed. The results are entered in table 5.

Example 18 (Comparative Example)

The base polymer I from example 17 was thermally surface postcrosslinked as in example 2. The fraction with a particle size of less than 710 μm was analyzed. The results are entered in table 6.

Example 19 (Comparative Example)

The procedure was as in example 11, except that the resulting polymer gel was not extruded. The base polymer J thus obtained was analyzed. The results are entered in table 5.

Example 20 (Comparative Example)

The base polymer J from example 19 was thermally surface postcrosslinked as in example 2. The fraction with a particle size of less than 710 μm was analyzed. The results are entered in table 6.

Example 21 (Comparative Example)

The procedure was as in example 13, except that the resulting polymer gel was not extruded. The base polymer K thus obtained was analyzed. The results are entered in table 5.

Example 22 (Comparative Example)

The base polymer K from example 21 was thermally surface postcrosslinked as in example 2. The fraction with a particle size of less than 710 μm was analyzed. The results are entered in table 6.

Example 23 (Comparative Example)

The procedure was as in example 15, except that the resulting polymer gel was not extruded. The base polymer L thus obtained was analyzed. The results are entered in table 5.

Example 24 (Comparative Example)

The base polymer L from example 23 was thermally surface postcrosslinked as in example 2. The fraction with a particle size of less than 710 μm was analyzed. The results are entered in table 6.

TABLE 5

Influence of crosslinker on the base polymer

| Ex. | Crosslinker [% by wt.] | CRC [g/g] | AUL0.3 psi [g/g] | FSR [g/gs] |
|---|---|---|---|---|
| 17*) | 0.20 | 38.0 | 8.9 | 0.33 |
| 19*) | 0.28 | 34.9 | 11.7 | 0.32 |
| 21*) | 0.35 | 34.2 | 13.8 | 0.31 |
| 23*) | 0.43 | 34.2 | 17.3 | 0.31 |

*)comparative examples

TABLE 6

Influence of crosslinker on the end product

| Ex. | Crosslinker [% by wt.] | SFC [$10^{-7} \times cm^3 s/g$] | CRC [g/g] | AUL0.7 psi [g/g] | FSR [g/gs] |
|---|---|---|---|---|---|
| 18*) | 0.20 | 152 | 26.4 | 23.6 | 0.18 |
| 20*) | 0.28 | 160 | 26.1 | 23.9 | 0.18 |
| 22*) | 0.35 | 138 | 25.9 | 23.7 | 0.20 |
| 24*) | 0.43 | 107 | 26.4 | 23.7 | 0.18 |

*)comparative examples

Examples 17 to 24 show that the amount of crosslinker used in the base polymers, in the absence of extrusion, does not have any significant influence on the free swell rate (FSR) after surface postcrosslinking.

Example 25 (Comparative Example)

The procedure was as in example 15, except that some of the polymer gel thus obtained was extruded with an OEE 8 extruder (AMANDUS KAHL GmbH & Co. KG; Hamburg; Germany). The temperature of the polymer gel in the course of extrusion was 85°. The perforated plate had 8 holes having a hole diameter of 8 mm. The thickness of the perforated plate was 15 mm. The ratio of internal length to internal diameter of the extruder (L/D) was 6.3. The specific mechanical energy (SME) of the extrusion was 89 kWh/t.

The base polymer M thus obtained was analyzed. The results are entered in table 7.

Example 26 (Comparative Example)

The base polymer M from example 25 was thermally surface postcrosslinked as in example 2. The fraction with a particle size of less than 710 μm was analyzed. The results are entered in table 8.

TABLE 7

Influence of SME on the base polymer

| Ex. | SME [kWh/t] | CRC [g/g] | AUL0.3 psi [g/g] | FSR [g/gs] |
|---|---|---|---|---|
| 15 | 26 | 32.5 | 22.9 | 0.40 |
| 25*) | 89 | 30.4 | 18.9 | 0.33 |

*)comparative example

TABLE 8

Influence of SME on the end product

| Ex. | SME [kWh/t] | SFC [$10^{-7} \times cm^3 s/g$] | CRC [g/g] | AUL0.7 psi [g/g] | FSR [g/gs] |
|---|---|---|---|---|---|
| 16 | 26 | 122 | 26.4 | 24.6 | 0.32 |
| 26*) | 89 | 133 | 25.9 | 24.7 | 0.26 |

*)comparative example

Examples 16 and 26 show that extrusion with excessively high specific mechanical energy (SME) lowers the free swell rate (FSR) after surface postcrosslinking.

The invention claimed is:

1. A process for producing water-absorbing polymer particles by polymerizing a monomer solution or suspension comprising
    a) an ethylenically unsaturated monomer which bears an acid group and may be at least partly neutralized,
    b) at least one crosslinker,
    c) at least one initiator,
    d) optionally an ethylenically unsaturated monomer copolymerizable with the monomer mentioned under a), and
    e) optionally one or more water-soluble polymer,
in a polymerization reactor having at least two shafts rotating in an axially parallel manner, drying the resulting polymer gel, grinding the dried polymer gel, classifying and thermally surface postcrosslinking, which process comprises using at least 0.25% by weight of the crosslinker b), based on the unneutralized monomer a), extruding the polymer gel through a perforated plate prior to drying, the polymer gel during the extrusion having a temperature greater than 80° C. and less than 60 kWh/t of specific mechanical energy being introduced in the course of extrusion, wherein the extruder has a ratio of length to diameter of less than 5.

2. The process according to claim 1, wherein the polymer gel during the extrusion has a temperature of greater than 90° C.

3. The process according to claim 1, wherein an orifice ratio of the perforated plate of the extruder is in the range from 10 to 20%.

4. The process according to claim 1, wherein a pressure bearing on the perforated plate of the extruder is in the range from 15 to 35 bar.

5. The process according to claim 1, wherein at least 0.4% by weight of the crosslinker b), based on the unneutralized monomer a), is used.

6. The process according to claim 1, wherein extrusion is effected through holes having a diameter of 8 to 12 mm.

7. The process according to claim 1, wherein the extruder is trace-heated.

8. The process according to claim 1, wherein at least 50 mol % of monomer a) is partly neutralized acrylic acid.

9. The process according to claim 1, wherein monomer a) has been neutralized to an extent of 25 to 85 mol %.

10. A process for producing water-absorbing polymer particles by polymerizing a monomer solution or suspension comprising
- a) an ethylenically unsaturated monomer which bears an acid group and may be at least partly neutralized,
- b) at least one crosslinker,
- c) at least one initiator,
- d) optionally an ethylenically unsaturated monomer copolymerizable with the monomer mentioned under a), and
- e) optionally one or more water-soluble polymer, in a polymerization reactor having at least two shafts rotating in an axially parallel manner, drying the resulting polymer gel, grinding the dried polymer gel, classifying and thermally surface postcrosslinking, which process comprises using at least 0.25% by weight of the crosslinker b), based on the unneutralized monomer a), extruding the polymer gel through a perforated plate prior to drying, the polymer gel during the extrusion having a temperature greater than 80° C. and less than 60 kWh/t of specific mechanical energy being introduced in the course of extrusion, wherein an orifice ratio of the perforated plate of the extruder is in the range from 10 to 20%.

11. The process according to claim 10, wherein the polymer gel during the extrusion has a temperature of greater than 90° C.

12. The process according to claim 10, wherein a pressure bearing on the perforated plate of the extruder is in the range from 15 to 35 bar.

13. The process according to claim 10, wherein extrusion is effected through holes having a diameter of 8 to 12 mm.

14. The process according to claim 10, wherein the extruder is trace-heated.

15. The process according to claim 10, wherein at least 50 mol % of monomer a) is partly neutralized acrylic acid.

16. A process for producing water-absorbing polymer particles by polymerizing a monomer solution or suspension comprising
- a) an ethylenically unsaturated monomer which bears an acid group and may be at least partly neutralized,
- b) at least one crosslinker,
- c) at least one initiator,
- d) optionally an ethylenically unsaturated monomer copolymerizable with the monomer mentioned under a), and
- e) optionally one or more water-soluble polymer, in a polymerization reactor having at least two shafts rotating in an axially parallel manner, drying the resulting polymer gel, grinding the dried polymer gel, classifying and thermally surface postcrosslinking, which process comprises using at least 0.25% by weight of the crosslinker b), based on the unneutralized monomer a), extruding the polymer gel through a perforated plate prior to drying, the polymer gel during the extrusion having a temperature greater than 80° C. and less than 60 kWh/t of specific mechanical energy being introduced in the course of extrusion, wherein a pressure bearing on the perforated plate of the extruder is in the range from 15 to 35 bar.

17. The process according to claim 16, wherein the polymer gel during the extrusion has a temperature of greater than 90° C.

18. The process according to claim 16, wherein extrusion is effected through holes having a diameter of 8 to 12 mm.

19. The process according to claim 16, wherein the extruder is trace-heated.

20. A process for producing water-absorbing polymer particles by polymerizing a monomer solution or suspension comprising
- a) an ethylenically unsaturated monomer which bears an acid group and may be at least partly neutralized,
- b) at least one crosslinker,
- c) at least one initiator,
- d) optionally an ethylenically unsaturated monomer copolymerizable with the monomer mentioned under a), and
- e) optionally one or more water-soluble polymer, in a polymerization reactor having at least two shafts rotating in an axially parallel manner, drying the resulting polymer gel, grinding the dried polymer gel, classifying and thermally surface postcrosslinking, which process comprises using at least 0.25% by weight of the crosslinker b), based on the unneutralized monomer a), extruding the polymer gel through a perforated plate prior to drying, the polymer gel during the extrusion having a temperature greater than 80° C. and less than 60 kWh/t of specific mechanical energy being introduced in the course of extrusion, wherein extrusion is effected through holes having a diameter of 8 to 12 mm.

* * * * *